Figure 1:
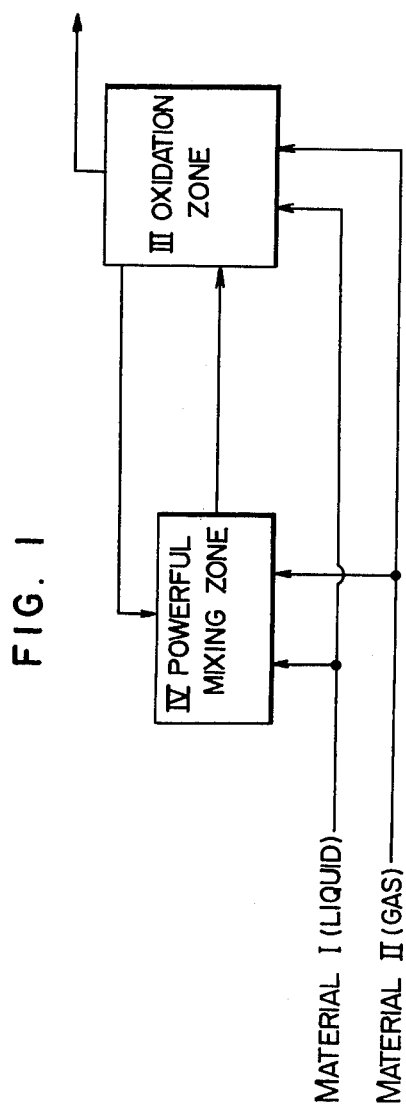

United States Patent [19]

Suda et al.

[11] 3,933,921

[45] Jan. 20, 1976

[54] PROCESS FOR THE PRODUCTION OF HYDROPEROXIDES

[75] Inventors: Hideaki Suda, Takaishi; Iwao Dohgane, Nishinomiya; Takashi Chinuki, Toyonaka; Kenji Tanimoto; Hirokazu Hosaka, both of Minoo; Yukimichi Nakao, Kobe; Yuji Ueda, Izumiotsu; Seiya Imada, Sakai; Hideki Yanagihara, Toyonaka; Kunihiko Tanaka, Ibaragi, all of Japan

[73] Assignee: Sumitomo Chemical Company, Limited, Osaka, Japan

[22] Filed: June 18, 1973

[21] Appl. No.: 370,673

[30] Foreign Application Priority Data

June 23, 1972 Japan............................ 47-63510

[52] U.S. Cl............................................. 260/610 B
[51] Int. Cl.² ............... C07C 179/02; C07C 179/04
[58] Field of Search ..................... 260/610 A, 610 B

[56] References Cited
UNITED STATES PATENTS

| | | | |
|---|---|---|---|
| 2,547,938 | 4/1951 | Holl et al. ....................... | 260/610 B |
| 2,548,435 | 4/1951 | Lorand et al..................... | 260/610 B |
| 2,619,510 | 11/1952 | Armstrong et al. ............. | 260/610 B |
| 2,632,026 | 3/1953 | Conner et al. ................... | 260/610 B |
| 2,632,772 | 4/1953 | Armstrong et al. ............. | 260/610 B |
| 2,632,773 | 4/1953 | Armstrong et al. ............. | 260/610 B |
| 2,632,774 | 3/1953 | Conner et al. ................... | 260/610 B |

*Primary Examiner*—James O. Thomas, Jr.
*Assistant Examiner*—W. B. Lone
*Attorney, Agent, or Firm*—Stevens, Davis, Miller & Mosher

[57] ABSTRACT

In a process for the production of hydroperoxides by the oxidation of an aromatic hydrocarbon having at least one tertiary carbon atom with oxygen or an oxygen containing gas in the presence of an aqueous alkaline solution, an improvement is made in that the oxidation is effected in an emulsion phase which is caused by powerfully mixing all or a part of the materials to be brought into the oxidation reaction only by the aid of the hydroperoxides formed in the reaction, whereby enhancing the reaction rate with safety.

6 Claims, 1 Drawing Figure

PROCESS FOR THE PRODUCTION OF HYDROPEROXIDES

The present invention relates to a method for producing a hydroperoxide of an aromatic hydrocarbon having at least one tertiary carbon atom.

An aromatic hydrocarbon hydroperoxide (referred to as HPO hereinafter) has been obtained by the following known methods.

1. An aromatic hydrocarbon is oxidized at 80° to 150°C in a liquid phase with an oxygen gas or air.
2. A mixture of an aromatic hydrocarbon and water is emulsified with the aid of emulsifier and then oxidized at 80° to 150°C with oxygen or air.

The former process can give the above mentioned HPO at a high reaction rate because the hydrocarbon is subjected directly to a high-temperature oxidation in a liquid phase, but there are such drawbacks in the process as rendering the product colored and necessify of controlling the reaction condition in order to avoid the formation of explosive mixture gases.

The latter process, on the contrary, can safely give a high-quality HPO, but there are drawbacks, too, such as a lower reaction rate and the difficulty of separating the oil and aqueous layers of the reaction mixture due to the emulsifier remaining therein, thereby causing a troublesome problem of after-treatment. Therefore the both processes should be said to have an advantage on one side but a disadvantage on the other side.

The inventors have made a study on the improvement of the latter process to increase the reaction rate without losing its superior advantages, and found that firstly hydroperoxides and/or hydroperoxide group-containing compounds resulting from an oxidation of aromatic hydrocarbon with an oxygen gas or air can act on oil and water as an emulsifier, secondly their emulsifying-effect can be best displayed by a mechanical forced mixing and therefore the addition of any emulsifier is not always necessary, and lastly the oxidation reaction in the emulsion phase thus formed can show very superior selectivity and reactivity, as compared with that of the conventional processes using emulsifiers. In other words, according to the present invention involving the use of a part of oxidation products as an emulsifier, there is provided a process for producing hydroperoxides safely and economically wherein the oxidation reaction is carried out in emulsion phase formed by mechanically and violently mixing all or a part of the reaction mixture consisting of an oily and an aqueous layers, and wherein the emulsion phase may be prepared in a reaction vessel, or in other apparatus followed by recycling to the reaction vessel.

In order to carry out efficiently an oxidation reaction involving oil, water and an oxygen-containing gas, it is necessary to prepare a uniform reaction mixture and to bring the gas and liquid into intimate contact. A conventional process for this purpose is to prepare an emulsion of oil and water by the aid of addition of emulsifier, or to violently mix the reaction mixture, both of which need a very large power of stirring. However, the inventors' study showed that the most important point of the oxidation reaction in emulsion phase is to renew and renovate interfaces rather than to form so much a stable emulsion state as formed with emulsifier.

Thus, the present invention is to provide a process for the production of hydroperoxides by the oxidation of an aromatic hydrocarbon having at least one tertiary carbon atom with oxygen or an oxygen containing gas in the presence of an aqueous alkaline solution, which comprises conducting the oxidation by powerfully mixing all or a part of a mixture containing the reaction mixture obtained from the aromatic hydrocarbon, oxygen or the oxygen containing gas and the alkaline aqueous solution, or all or a part of a mixture containing the aromatic hydrocarbon and the alkaline aqueous solution together with a part of oxygen or the oxygen containing gas or without oxygen or the oxygen containing gas, to emulsify the mixture.

Aromatic hydrocarbons of the present invention having at least one tertiary carbon atom include cumene, cymene, butylbenzene, diisopropyltoluenes, diisopropylbenzenes, isopropylnaphthalenes, diisopropylnaphthalenes and the like.

The feature of the present invention resides in to carry out the oxidation reaction in an emulsion of oil and the minimum amount of water being formed by means of powerful mechanical mixing, whereby increasing the oxidation rate to produce HPO with a high purity and preventing any danger of explosion.

The amount of an aqueous layer to be mixed with an aromatic hydrocarbon (an oily layer) is more than one-thirtieth based on the oily layer, and preferably more than one-tenth. Although one of the features of the invention is to make it possible to decrease the amount of aqueous layer to be used, when it is less than one-thirtieth an emulsion state thus formed is not suitable for the oxidation in some cases. A remarkably increased proportion of the aqueous layer to the oily layer, on the contrary, makes the formed emulsion state unstable thereby separating the aqueous layer therefrom, and a retention time of the oily layer is shortened, whereby a loss of products increases due to the transfer of oxidation products into the aqueous layer and a problem of waste water treatment occurs. Therefore, from an economical point of view, the preferred amount of the aqueous layer is within a range of from one-tenth to equal to the amount of the oily layer.

A mechanical powerful mixing may be carried out to such an extent that a formed emulsion state is stable enough to make possible the formation of fresh or active interfaces, but not unstable enough not to permit the oxidation reaction to proceed.

The mechanical powerful mixing to prepare the emulsion state may be performed, for example, by the following mixers: a mixing pump, a two-fluid nozzle, an immovable type mixer (e.g., commercially available "static mixer" or "dynamic mixer"), a double-arm heavy duty dispersion mixer such as various types of masticator machine which includes a pressure type (e.g., a Banbury mixer, dispersion mixer or MS-type heavy duty pressure kneader) and a normal type (e.g., a heavy duty double-arm kneader, universal kneader or heavy duty kneader), and a cavitator.

The mixture to be mechanically mixed may be all or a part of the materials to be brought into the oxidation reaction. More concretely speaking, the mixture may be a mixture of oily layer and aqueous layer, or a mixture containing an oxygen-containing gas together with the both layers. The emulsified mixture prepared by those means is different from a conventional one prepared chemically by the addition of emulsifier, and so it has not disadvantages that the aqueous layer is difficultly separable from the oily layer in an after-treatment, and that the resulting by-products are transferred into the oily layer. As to the general conditions of the oxidation reaction such as the kind of alkali used, the concentration thereof in the aqueous layer, pH of the aqueous layer containing emulsified aromatic hydrocarbons, reaction time and reaction temperature, well known conditions may be used. For example, the oxidation can be effected at a temperature of 80° to 150°C, preferably at 90° to 120°C, for 1 to 30 hours, usually 5 to 20 hours, while pH of the mixture being kept to 5 to 12, preferably 9 to 10 by use of an alkali, such as sodium hydroxide and sodium carbonate, in an amount of 0.1 to 5 % by weight based on the amount of the oily layer.

One of the features of the present invention is, as clearly described above, to prepare an emulsion by using the products resulting from the reaction, and so the process according to the present invention becomes more advantageous as the conversion in the reaction becomes higher. Therefore it is a matter of course that the process becomes more effective in a continuous operation of this type of oxidation reaction.

A conventional mixing process in this kind of reaction is intended to bring a gas and a liquid (an oily and an aqueous layers) into contact. For this purpose, it has hitherto been tried to obtain a good dispersion of gas in liquid by use of various apparatus such as a perforated plate or a dispersion plate, or by improvements of a stirrer, a blowing technique or a mixing nozzle. Alternatively, it has also been tried by modification of the oxidation conditions such as a pressure, and a volume, linear velocity and bubble size of gas to be blowed. Contrary to this, the mechanical powerful mixing of the present invention is intended to mix an oily layer and an aqueous layer constituting a mixture to be reacted, but not to disperse a gas into the mixture. Therefore, as a matter of course, there exists a large difference between the procedures of the two processes, and the conventional process involves a gas as an essential factor, on the other hand what is important in the process of the invention is the mixing of an oily layer with an aqueous layer, but not the dispersion of gas. Because of this difference, the mixing may be carried out anywhere, e.g., in a reactor, or out of a reactor, irrespective of the presence of gas. With a conventional mean which is intended to disperse a gas in a liquid, it will be impossible or substantially impossible to expect the mixing effect comparable to that of a mechanical powerful mixing without using a mean which is not economical. In this way, the inventors have found that the most important point for carrying out the oxidation reaction effectively is to mix the two layers, each constituting the reaction liquid, so as to reveal constantly fresh or active interfaces and not necessarily to disperse a gas in a liquid, and that products themselves resulting from the oxidation reaction is most suitable for the formation of the emulsion state. The inventors have accomplished the mechanical powerful mixing process of the invention based on the above discovery.

One example of the reaction system according to the mechanical powerful mixing of the invention will be explained by referring to the attached drawing, in which FIG. 1 shows a schematic flow-sheet of an example of the invention. A liquid material I and a gaseous material II are fed to oxidation zone III, the material I comprising as major components an aromatic hydrocarbon (oily layer) having at least one tertiary carbon atom and an aqueous layer, and in addition a catalyst and a small amount of additives, and the material II comprising an oxygen gas or/and air in most cases. The oxidation reaction mixture and all or a part of the gas are fed from the oxidation zone III to a powerful mixing zone IV where they are subjected to a mechanical powerful mixing by the apparatus previously mentioned. The resulting emulsion is fed back to the oxidation zone III. In addition to the main stream of the materials as shown herein, all or a part of the material I may be fed to the powerful mixing zone IV together with a part of the material II or without the material II (that is, all of the material II is fed to the oxidation zone). Alternatively, one zone may have the combined function of the oxidation zone III and the mechanical mixing zone, IV, i.e., the function of the oxidation and emulsification. The process of the invention can most effectively be applied to the production of hydroperoxides from alkylbenzenes in order to prepare resorcin and hydroquinone.

The present invention will be illustrated in more detail with reference to the following examples, which are only illustrative, but not limitative.

EXAMPLE 1

To 150 kg. of cymene were added 50 kg. of water dissolving 3 kg. of caustic soda, and then 3 kg. of oxidized cymene oil containing 60 % cymenehydroperoxide as a reaction initiator, and 800 g. of stearic acid as an emulsifier, were added thereto. The resulting mixture was oxidized at 100°C. by passing therethrough a compressed air of 5 atms, at a rate of 20 $Nm^3/hr$.

The reaction was carried out in a 500-l cylindrical vessel made of stainless equipped with a gas-dispersion apparatus, a thermometer, an air-introducing pipe and an overhead condenser for the vapour of reaction mixture leaving the vessel with air. Test samples of reaction mixture were withdrawn at the regular time intervals and analyzed according to a normal procedure. The results were as follows:

| Reaction time (hr.) | HPO content in oxidation solution (concentration by weight) |
|---|---|
| 2 | 3.9 % |
| 4 | 7.1 % |
| 6 | 11.1 % |
| 8 | 14.9 % |
| 10 | 19.4 % |

An oxidation yield after 10 hours (a percentage by mol of HPO produced based on cymene consumed) was 62.8 %.

Next, the reaction was carried out in such a recycle process that a part of reaction mixture in the vessel was passed to a circulating pump at a rate of 20 l/min. where it was forced to be mixed mechanically, and then was passed back to the vessel. All other reaction conditions were the same as defined above except that an emulsifier was not used. The results obtained were as follows:

| Reaction time (hr.) | HPO % |
|---|---|
| 2 | 4.6 |
| 4 | 11.4 |
| 6 | 19.8 |
| 8 | 24.6 |

An oxidation yield after 8 hours was 78.3 %.

EXAMPLE 2

To 160 kg. of cumene, were added 50 kg. of water containing 5.4 kg. of sodium carbonate, 2.1 kg. of oxidized cumene oil containing 80 % of cumene hydroperoxide and 1.2 kg. of stearic acid. The resulting mixture was oxidized in the same vessel (without a circulating pump) as in Example 1 at 120°C by passing therethrough a compressed air of 7 atoms, at a rate of 30 Nm$^3$/hr. Test samples of reaction solution were withdrawn at the regular time intervals and analyzed. The results were as follows:

| Reaction time (hr.) | HPO (%) in oxidation solution |
| --- | --- |
| 4 | 8.1 |
| 8 | 15.4 |
| 12 | 22.2 |
| 16 | 31.2 |
| 20 | 40.5 |

An oxidation yeild after 20 hours was 84.2 %.

The reaction mixture (containing no stearic acid) prepared similarly as in the above case was charged in the vessel equipped with a circulating pump, and was oxidized under the same conditions as defined above while it was recycled through pump to the vessel at a rate of 25 l/min. The results obtained were as follows:

| Reaction time (hr.) | HPO (%) |
| --- | --- |
| 4 | 7.9 |
| 6 | 15.4 |
| 8 | 21.5 |
| 10 | 28.8 |
| 12 | 35.3 |
| 14 | 41.7 |

An oxidation yield after 12 hours was 89.1 %.

REFERENTIAL EXAMPLE

The following experimental results were obtained with a liquid-phase oxidation using no emulsifier. From the results it can be observed that the liquid-phase oxidation process gives a high rate of production of HPO but a low yield thereof, and that the process according to the invention gives the same rate as that obtained with the liquid-phase oxidation.

The reaction was carried out under the same conditions as in Example 2 except that water was not used. The results were as follows:

| Reaction time (hr.) | HPO (%) |
| --- | --- |
| 4 | 8.1 |
| 6 | 18.4 |
| 8 | 31.9 |
| 10 | 35.2 |
| 12 | 32.7 |

An oxidation yield after 10 hours was 77.4 %.

EXAMPLE 3

To the same vessel were added 150 kg. of sec. butylbenzene, 70 kg. of water containing 2.5 kg. of caustic soda, 1.4 kg. of an emulsifier and some amount of a reaction-initiator. The resulting mixture was oxidized at 120°C while a compressed air of 6 atoms was passed therethrough in an amount of more than two times that required to produce hydroperoxide. The results obtained were as follows.

| Reaction time (hr.) | HPO % in oxidation solution |
| --- | --- |
| 4 | 3.2 |
| 8 | 7.5 |
| 12 | 13.1 |
| 16 | 20.9 |
| 20 | 25.4 |

An oxidation yield after 20 hours was 65.8 %.

The oxidation reaction was carried out in such a recycle process that part of the reaction mixture withdrawn from the vessel and part of the compressed air were mixed mechanically through a two-liquid nozzle and a line connecting thereto, and then passed back to the vessel. The amount of the solution which was passed through the nozzle was 20 l/min. All other conditions were the same as discribed above. The results obtained were as follows:

| Reaction time (hr.) | HPO (%) |
| --- | --- |
| 4 | 3.2 |
| 8 | 13.3 |
| 12 | 25.4 |
| 16 | 31.8 |

An oxidation yield after 12 hours was 74.7 %.

EXAMPLE 4

To 150 kg. of diisopropylbenzene were added 15 kg. of water containing 200 g. of caustic soda, 200 g. of stearic acid as an emulsifier, and 2 kg. of oxidized oil containing 70 % of hydroperoxide as a reaction-initiator. The reaction was carried out in the same way as in Example 1. And the effects of emulsification by an emulsifier and by a mechanical forced mixing on the oxidation reaction were observed. In the latter case, stearic acid was not used. The results obtained were as follows:

| Reaction time | Emulsifier | | Mechanical mixing | |
| --- | --- | --- | --- | --- |
| | Total HPO*1 | di-HPO*2 | Total HPO*1 | di-HPO*2 |
| (hour) | (% by weight) | (") | (") | (") |
| 3 | 28.14 | 2.63 | 34.09 | 2.60 |
| 6 | 48.71 | 8.97 | 74.19 | 22.81 |
| 8 | 57.99 | 12.02 | 96.06 | 27.50 |
| 10 | 66.41 | 16.20 | 115.41 | 30.90 |
| 12 | 77.04 | 22.62 | | |

Remarks:
*1 All hydroperoxides contained in the oxidation solution were converted to a monohydroperoxide basis.
*2 Dihydroperoxide contained in the oxidation mixture.

What we claim is:

1. In a process for the production of hydroperoxides by the oxidation of an aromatic hydrocarbon having at least one tertiary carbon atom selected from the group consisting of cumene, cymene, butylbenzene, diisopropyltoluene, diisopropylbenzene, isopropylnaphthalenes and diisopropylnaphthalenes with oxygen or an oxygen containing gas in the presence of an aqueous alkaline solution, at a temperature of 80° to 150°C and at pH of 5 to 12, the improvement which comprises conducting the oxidation by forming an emulsion phase by powerfully mixing at least part of said aromatic hydrocarbons and said aqueous alkaline solution, said mixing being performed by powerfully mixing an intermediate reaction mixture obtained after the oxygen has initially reacted with the aromatic hydrocarbon and containing said aqueous alkaline solution.

2. In a process for the production of hydroperoxides by the oxidation of a mononuclear or binuclear aromatic hydrocarbon having at least one tertiary carbon atom with oxygen or an oxygen containing gas in the presence of an aqueous alkaline solution at a temperature of 80° to 150°C and at pH of 5–12, the improvement which comprises conducting the oxidation by forming an emulsion phase by powerfully mixing at least part of said aromatic hydrocarbon and said aqueous alkaline solution, said mixing being performed by powerfully mixing an intermediate reaction mixture obtained after the oxygen has initially reacted with the aromatic hydrocarbon and containing said aqueous alkaline solution.

3. In a process for the production of hydroperoxides by the oxidation of an aromatic hydrocarbon having at least one tertiary carbon atom selected from the group consisting of cumene, cymene, butylbenzene, diisopropyltoluene, diisopropylbenzene, isopropylnaphthalenes and diisopropylnaphthalenes with oxygen or an oxygen containing gas in the presence of an aqueous alkaline solution, at a temperature of 80° to 150°C and at pH of 5 to 12, the improvement comprising conducting the oxidation upon an emulsion phase formed by powerfully mixing at least part of said aromatic hydrocarbon and said aqueous alkaline solution, said mixing being performed by powerfully mixing a mixture of the unreacted aromatic hydrocarbon, the aqueous alkaline solution and the oxygen.

4. In a process for the production of hydroperoxides by the oxidation of an aromatic hydrocarbon having at least one tertiary carbon atom selected from the group consisting of cumene, cymene, butylbenzene, diisopropyltoluene, diisopropylbenzene, isopropylnaphthalenes and diisopropylnaphthalenes with oxygen or an oxygen containing gas in the presence of an aqueous alkaline solution at a temperature of 80° to 150°C and at pH of 5 to 12, the improvement comprising conducting the oxidation upon an emulsion phase formed by powerfully mixing at least part of said aromatic hydrocarbon and said aqueous alkaline solution, said mixing being performed by powerfully mixing a mixture of the unreacted aromatic hydrocarbon and the aqueous alkaline solution.

5. In a process for the production of hydroperoxides by the oxidation of a mononuclear or binuclear aromatic hydrocarbon having at least one tertiary carbon atom with oxygen or an oxygen containing gas in the presence of an aqueous alkaline solution at a temperature of 80° to 150°C and at pH of 5 to 12, the improvement which comprises conducting the oxidation by forming an emulsion phase by powerfully mixing at least part of said aromatic hydrocarbon and said aqueous alkaline solution, said mixing being performed by powerfully mixing a mixture of the unreacted aromatic hydrocarbon, the aqueous alkaline solution and the oxygen.

6. In a process for the production of hydroperoxides by the oxidation of a mononuclear or binuclear aromatic hydrocarbon having at least one tertiary carbon atom with oxygen or an oxygen containing gas in the presence of an aqueous alkaline solution at a temperature of 80° to 150°C and at pH of 5–12, the improvement which comprises conducting the oxidation by forming an emulsion phase by powerfully mixing at least part of said aromatic hydrocarbon and said aqueous alkaline solution, said mixing being performed by powerfully mixing a mixture of the unreacted aromatic hydrocarbon and the aqueous alkaline solution.

* * * * *